US00PP17249P3

(12) United States Plant Patent
Kelz

(10) Patent No.: US PP17,249 P3
(45) Date of Patent: Nov. 28, 2006

(54) *QUERCUS VIRGINIANA* TREE NAMED 'K-1'

(50) Latin Name: *Quercus virginiana*
Varietal Denomination: K-1

(76) Inventor: John Kelz, 2905 Joe Ashton Rd., Saint Augustine, FL (US) 32092

( * ) Notice: Subject to any disclaimer, the term of this patent is extended or adjusted under 35 U.S.C. 154(b) by 0 days.

(21) Appl. No.: 11/159,425

(22) Filed: Jun. 23, 2005

(65) Prior Publication Data

US 2005/0235389 P1 Oct. 20, 2005

(51) Int. Cl.
*A01H 5/00* (2006.01)

(52) U.S. Cl. ..... Plt./225
(58) Field of Classification Search ..... Plt./225
See application file for complete search history.

(56) References Cited

U.S. PATENT DOCUMENTS

PP11,219 P * 2/2000 Strickland ..... Plt./225
PP12,015 P2 * 7/2001 Reeves ..... Plt./225
2005/0235389 P1 * 10/2005 Kelz ..... Plt./225

* cited by examiner

*Primary Examiner*—Wendy Haas
(74) *Attorney, Agent, or Firm*—Jondle & Associates P.C.

(57) ABSTRACT

A new and distinct variety of *Quercus virginiana* tree named 'K-1' is disclosed. It is characterized by having a dense, upright naturally columnar habit, by being easily trained to a single leader, and by having small lateral branches leaving the main trunk at 45 degree angles and arching upward to produce a very compact and dense canopy. Its leaves are not shed noticeably in the spring, giving the appearance of an evergreen Live Oak.

3 Drawing Sheets

Genus/species: *Quercus virginiana.*
Variety denomination: 'K-1'.

BACKGROUND OF THE INVENTION

The present invention relates to a new and distinct variety of *Quercus virginiana* oak tree named 'K-1'. The genus *Quercus* is included in the family Fagaceae which comprises about six to nine genera and over 600 species of monoecious trees and shrubs most commonly found on the lower coastal plains of the southeastern United States. Of the five genera indigenous to North America, two are native to Florida. Oak is a fast-growing, yet very long-lived tree which can grow up to 50 feet in height. Once established, it withstands competition and is extremely tolerant to high alkalinity. This resistance may account for its dominance in many climax coastal forests in the northern part of its range.

Applicant discovered the new 'K-1' cultivar among 10,000 seedlings. The seedlings were planted in February of 1997 in three-gallon containers under overhead irrigation and grown for eighteen months at Kelz Nursery in Saint Augustine, Fla. 'K-1' became noticeable during the winter of 1998 when it was approximately 36 inches tall. In contrast to the other oak trees in this group, 'K-1' lost significantly fewer leaves, grew slightly taller and narrower, and exhibited dense and compact foliage. 'K-1' was planted in the ground in October of 2001, where it has performed the same each year.

SUMMARY OF THE INVENTION

The present invention relates to a new and distinct variety of *Quercus virginiana*, hereinafter referred to by the varietal name, 'K-1'. It is characterized by having a dense, upright naturally columnar habit, by being easily trained with a single leader, by having small lateral branches leaving the main trunk at 45 degree angles which produces a very compact and dense canopy. Moreover, its leaves are not shed noticeably in the spring, giving the appearance of an evergreen Live Oak. 'K-1' trees have been observed to grow about 3.5–4.5 feet per year when planted in containers or 2.0–2.5 feet per year when planted in the ground. The trunk calliper increases at 0.75 inches per year when planted containers, or 1.0 inches per year when planted in the ground. 'K-1' has been repeatedly asexually reproduced by stem cuttings at the Kelz Nursery in Saint Augustine, Fla. The distinctive characteristics of the new variety are stable and transmitted to succeeding generations; the new variety reproduces true to type in successive generations of asexual propagation. 'K-1' has not been observed under all growing conditions and as a result, variations may occur. All observations are of trees growing at Kelz Nursery, in Saint Augustine, Fla.

BRIEF DESCRIPTION OF THE ILLUSTRATIONS

This new oak tree is illustrated by the photographs which show the tree's form and foliage. The colors shown are as true as can be and reasonably obtained by conventional photographic procedures.

DETAILED DESCRIPTION OF THE NEW PLANT

Figure 1:
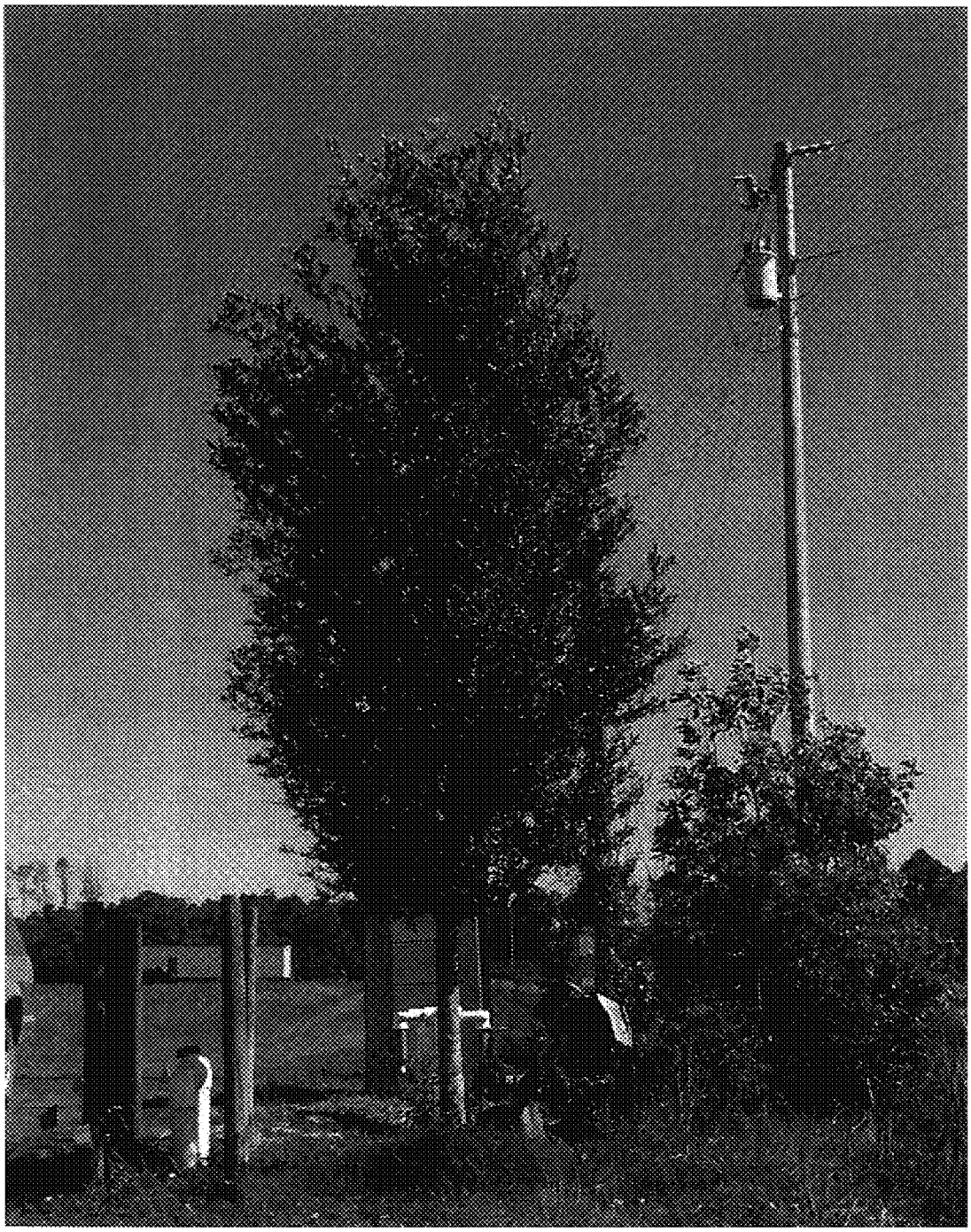
FIG. 1 depicts the overall columnar habit of the parent 'K-1' tree in the spring of 2004.
Figure 2:
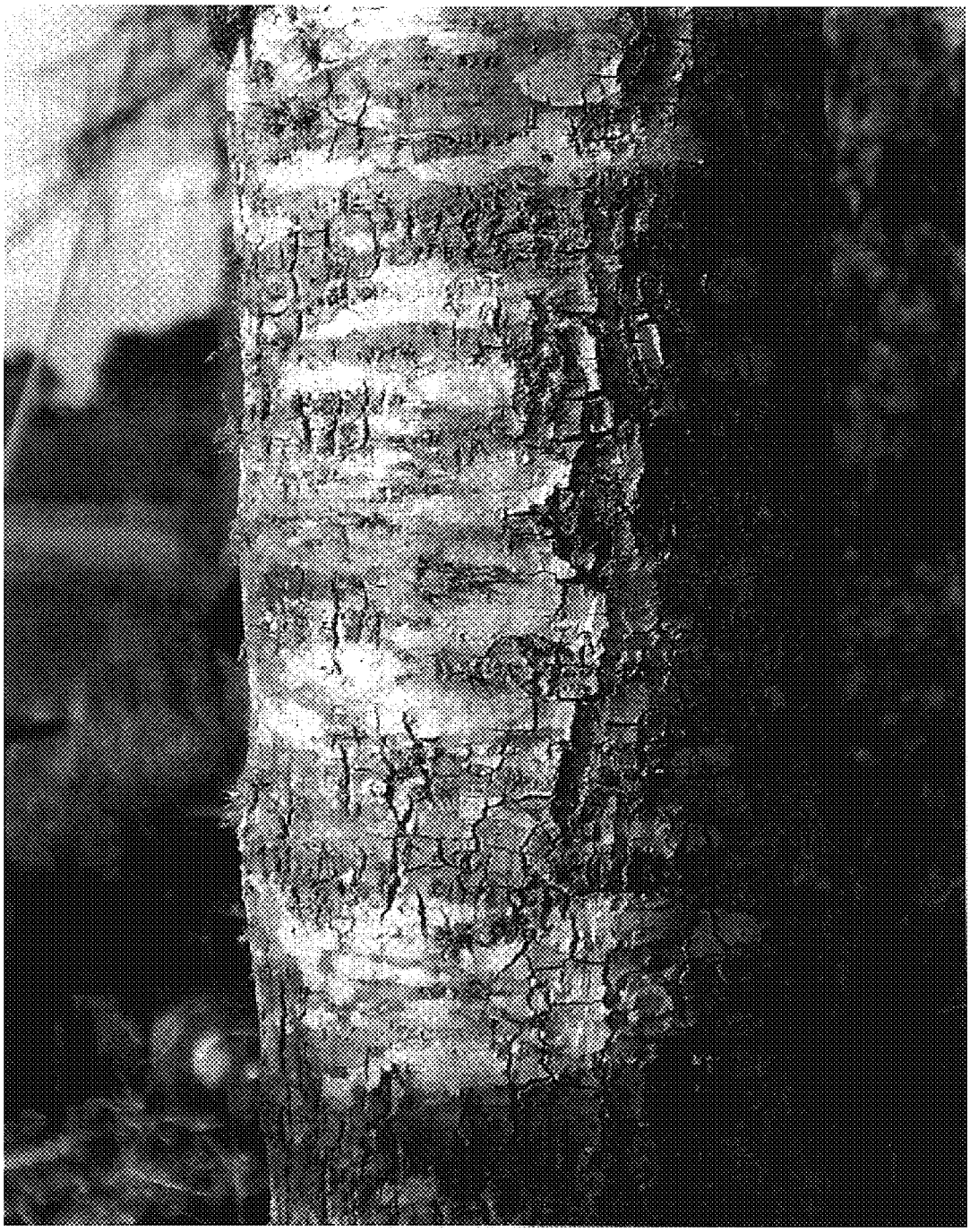
FIG. 2 depicts the bark of the parent 'K-1' tree.
Figure 3:
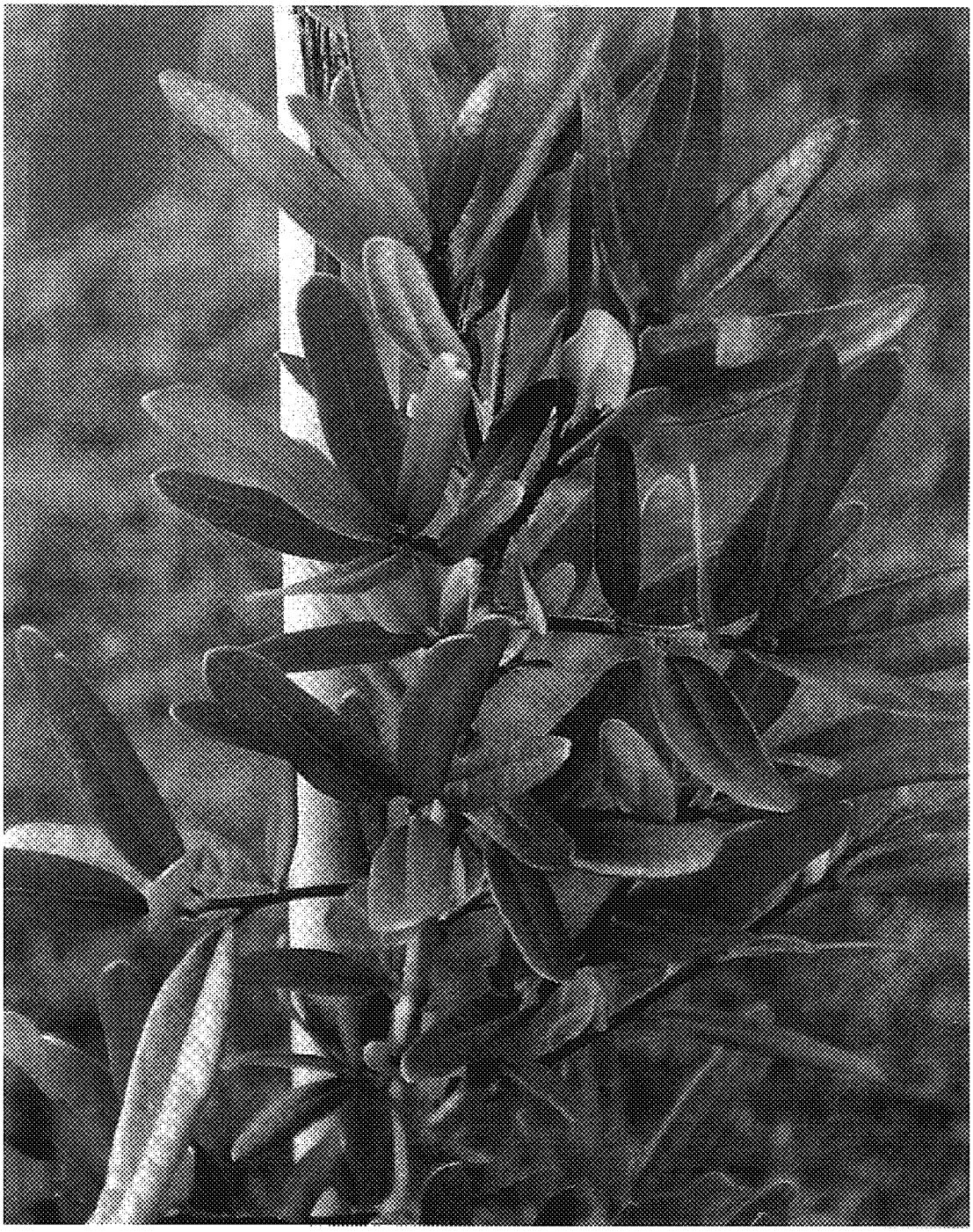
FIG. 3 depicts new spring growth, from nursery stock of parent 'K-1' tree, in a container.

The following detailed description of the new variety of oak is based on observations made of an 8 year-old tree grown according to wholesale commercial production conditions in Saint Augustine, Fla. The colors of the various plant parts are detailed with reference to The Royal Horticultural Society Colour Chart.

Classification:

*Origin/parentage.*—Unknown.

*Botanical name.*—*Quercus virginiana.*

*Common name.*—Live Oak.

Trunk:

*Size/calliper.*—At 8 years of age, average diameter of trunk is 5.5 inches measured at 12.0 inches above the ground.

*Bark.*—Color: Mottled RHS 197A (greyed-green) and 198D (greyed-green).

*Height.*—18.5 feet at 8 years of age.

*Growth habit or form.*—Upright and columnar habit with a single, straight strong central leader when young and remaining dominant. Dense habit is apparently due to closely held secondary branching and heavy leaf growth.

*Growth rate.*—3.5–4.5 feet per year when planted in containers and 2–2.5 feet per year when planted in the ground.

Branches:

*Angle of attachment.*—45 degrees.

*Spacing.*—8.0 inches.

*Size.*—Crown diameter of tree is 7.7 feet at 8 years.

*Color.*—RHS 197B for young trees and mature branches and RHS 178A for emerging branches.

*Size.*—Branches aged 8 years: Length: 6.0–6.5 feet. Diameter: 0.75–1.0 inches at about 6 inches from the trunk.

Leaves: Leaves are typical of *Quercus virginiana.*

*Arrangement.*—Alternate, simple.

*Shape.*—Elliptic to oblong or obovate.

*Base.*—Cuneate to rounded.

*Apex.*—Typically acute, sometimes obtuse.

*Venation.*—Prominent mid-rib beneath with 8 to 13 veins colored RHS 144C (yellow green).

*Margin.*—Entire with occasional acute lobes or teeth.

*Texture.*—Slightly tomentose on underside and stiff.

*Color.*—Emerging: Upper surface: RHS 151A (yellow-green). Lower surface: RHS 151B. Margin: RHS 61B (red-purple). Young-late spring: Apex: RHS 137A (greyed-orange). Base: RHS 144A (yellow-green). Mature to summer: Upper surface: RHS 137A (green). Lower surface: RHS 137C (green).

*Size.*—Small leaf: Width: 0.31 inches. Length: 1.5 inches. Number of veins: 8 veins. Medium leaf: Width: 0.75 inches. Length: 2.38 inches. Venation: Lobed with 9 veins. Large leaf: Width: 0.69 inches. Length: 2.88 inches. Number of veins: 9 to 11 veins.

*Petiole.*—Length: 0.065 inches for a mature leaf. Color: RHS 178A (greyed-red).

Reproductive organs: *Quercus virginiana* is typically monoecious. Generally, male catkins to 3 inches long are produced while pistillate flowers are fewer in number on long peduncles. Fruit consists of acorns.

Flowers: Typical of *Quercus virginiana*, with female flowers appearing in the axils.

Catkins: Have not been observed in this variety.

Fruit:

*Type.*—Acorn, appearing singly or in clusters.

*Color.*—First ring at 0.06 inches: RHS 159C (greyed-orange). Second ring at 0.13 inches: RHS 164C (greyed-orange). Third ring at 0.25 inches: RHS N199B (greyed-brown). At 0.5 inches: the acorn is RHS 200A (brown) and culminating to a point approximately 0.06 inches in length and RHS N199B (greyed-brown).

*Shape.*—Oblong to ellipsoid.

*Apex.*—Pointed.

*Length.*—1 inch at maturity.

*Width.*—0.88 inches at maturity and at widest point.

*Involucres.*—Turbinate.

*Ridges.*—Run the length of the acorn.

Disease and pest susceptibility/resistance: Has not been observed.

What is claimed is:

1. A new and distinct variety of *Quercus virginiana* tree named 'K-1' as shown and described herein.

* * * * *